US006093164A

United States Patent [19]

Davis et al.

[11] Patent Number: 6,093,164

[45] Date of Patent: Jul. 25, 2000

[54] VIBRATORY SLEEVE AND METHOD FOR THE TREATMENT OF REPETITIVE TRAUMA SYNDROME

[75] Inventors: William M. Davis, 730 Shady Hollow La., Akron, Ohio 44313; Mark J. Yanke, Akron, Ohio

[73] Assignee: William M. Davis, Akron, Ohio

[21] Appl. No.: 09/118,226

[22] Filed: Jul. 17, 1998

[51] Int. Cl.[7] .............................. A61F 13/00; A61F 5/00; A61H 1/00

[52] U.S. Cl. .................................. 602/62; 602/5; 602/20; 602/60; 602/61; 601/46; 601/48

[58] Field of Search .......................... 602/60–79; 607/46, 607/48, 149, 151, 152; 601/46, 48, 70, 71, 72, 74, 79, 80

[56] References Cited

U.S. PATENT DOCUMENTS 5,575,761 11/1996 Hajianpour ................................ 601/48

*Primary Examiner*—Kim M. Lee

*Attorney, Agent, or Firm*—Renner, Kenner, Greive, Bobak, Taylor & Weber

[57] ABSTRACT

A device for the delivery of low amplitude vibration to limbs comprises a flexible sleeve adaptable to fit circumferentially around the limb of a living being; means for mounting the sleeve about the limb; means for generating a low amplitude vibration, carried by said sleeve; and means for transmitting the vibrations to said limb. A method for the treatment of repetitive trauma syndrome comprises affixing a device providing a flexible sleeve circumferentially about the limb affected and transmitting a low amplitude vibration from the device to the limb.

18 Claims, 4 Drawing Sheets

VIBRATORY SLEEVE AND METHOD FOR THE TREATMENT OF REPETITIVE TRAUMA SYNDROME

TECHNICAL FIELD

This present invention provides a vibratory sleeve which can be worn in the work place and/or at rest to decrease the effect of repetitive trauma to the anatomical structures of the forearm which in turn causes pain, limitation of normal movement and compromised performance of vocational and avocational activities. The vibratory sleeve can be used both in stationary and ambulatory activities as it is capable of either battery or AC/DC activation. It is recommended for either prophylactic or acute symptom alleviation. The present invention also provides a method for treating repetitive or cumulative trauma syndrome.

BACKGROUND OF THE INVENTION

Repetitive trauma syndrome (RTS) is well documented in the literature and is a common diagnosis in the charts located in orthopaedic and rehabilitation offices across the world, and has proliferated with the popularity of computers, both at work and at home. Modalities directed toward the treatment and/or infringement of pain and discomfort associated with repetitive trauma syndrome (RTS) or overuse syndrome employ various splints, physical and/or occupation therapy, massage, heat and cold packs and/or exercise(s) in various combinations. The ultimate mode of treatment is surgery, which does not assume a curative role but offers some degree of immediate relief. All of these modalities either restrict activities and/or remove the afflicted from the work place or from avocational activities for prescribed times of treatment.

Carpal tunnel syndrome (CTS) is one of the most prevalent of the repetitive trauma maladies and treatment employs the traditional modalities outlined hereinabove. Therefore, limitations of activities and time constraints are placed upon the afflicted person, whereas the device of the present invention does not further compromise the afflicted; wrists and hands are free, the device is contoured for a comfortable fit and there is neither weight nor bulk to confound the wearer. The wearer does not have to leave the work place for prescriptive therapies or more constrictive modalities.

The device of the present invention is also not offensive to others who work or engage in avocational activities with the wearer. Splints utilized in the treatment of CPS generally involve the hand and thus, frequently become soiled and can be both visually offensive due to their appearance and could pose hygienic problems to both the wearer and surrounding items or those with whom there is physical contact. Restrictive devices also can cause an awkwardness in movement which can affect not only the activities of the wearer but those with whom there is interaction.

The patent literature does include a variety of wearable devices or splints for the treatment of CTS and related disorders. A flexible wrist splint for such disorders is described in U.S. Pat. No. 4,854,309. While effective in the treatment of CTS, this splint does not provide any vibratory treatment or therapy.

SUMMARY OF THE INVENTION

It is therefore, an object of the present invention to provide a vibratory sleeve to alleviate the symptoms associated with repetitive trauma syndrome.

It is another object of the present invention to provide a vibratory sleeve that is versatile in use, thereby adjusting to both an ambulatory or stationary activity.

It is yet another object of the present invention to provide a comfortable and effective fit to the human forearm by means of a multilayered contoured sleeve which is secured by adjusting Velcro straps to the wearer's level of comfort.

It is still another object to decrease the number of the more invasive and/or expensive medical modalities used in the treatment of RTS.

It is another object of this invention to decrease symptoms and/or eliminate symptoms of RTS and allow people to pursue vocational and avocational activities as they desire.

It is yet another object of the present invention to provide a method for the treatment of repetitive trauma syndrome.

It is still another object of this invention to provide a method that is comfortable, easy to use, and provides the ability to use while the wearer is engaged in normal activity.

At least one or more of the foregoing objects together with the advantages thereof over the prior art, which shall become apparent from the specification which follows, are accomplished by the invention as hereinafter described and claimed.

In general, a device for the delivery of low amplitude vibration to limbs according to the present invention comprises a flexible sleeve adaptable to fit circumferentially around the limb of a living being; means for mounting the sleeve about the limb; means for generating a low amplitude vibration, carried by the sleeve; and means for transmitting the vibrations to the limb.

A method for the treatment of repetitive trauma syndrome, according to the present invention comprises affixing a device providing a flexible sleeve circumferentially about the limb affected and transmitting a low amplitude vibration from said device to said limb.

PREFERRED EMBODIMENT FOR CARRYING OUR THE INVENTION

Figure 1:
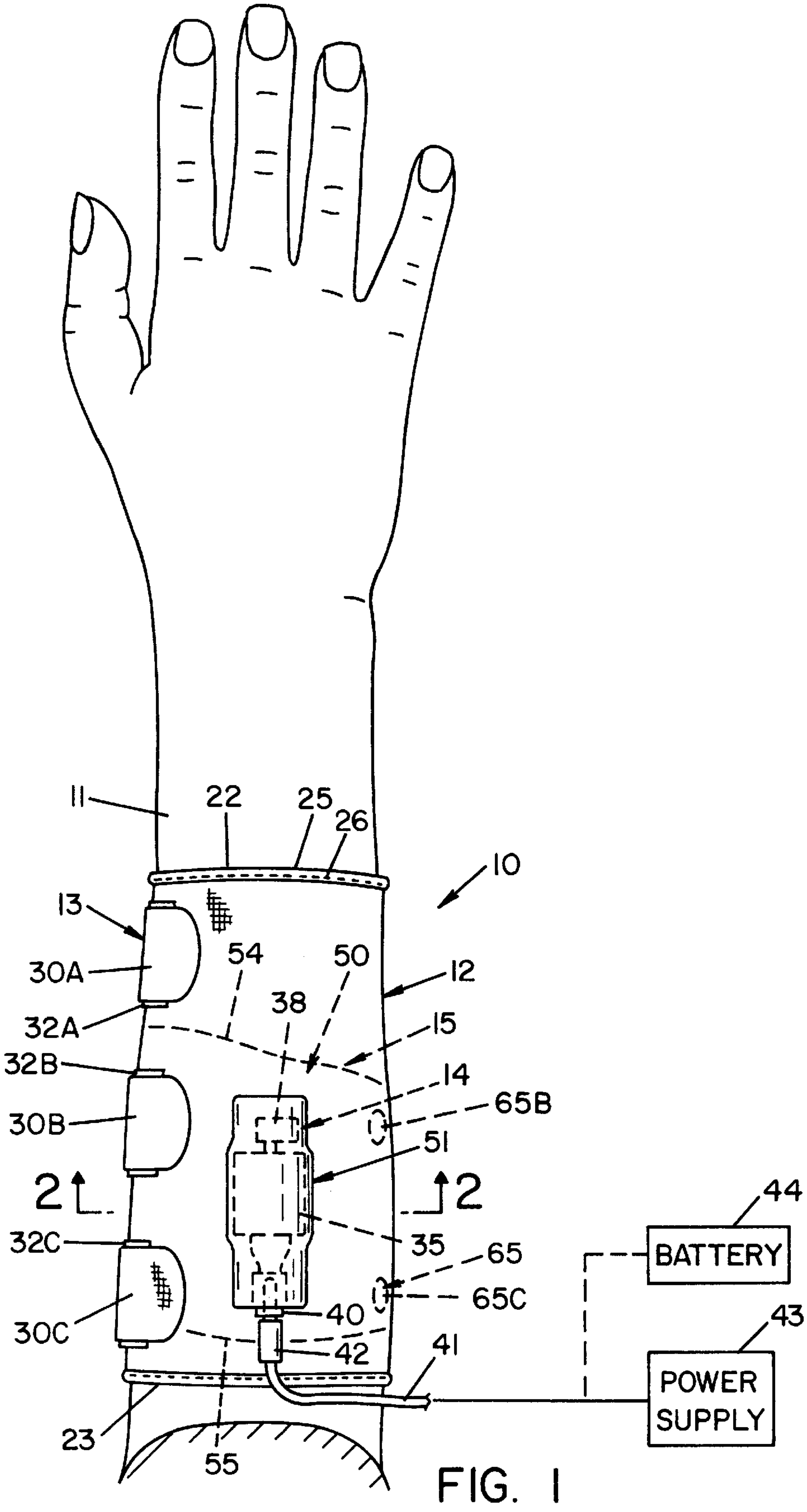
FIG. 1 is a top plan view of the vibratory sleeve of the present invention, positioned on the forearm.

The present invention provides a device for supporting soft tissues while anatomical structures in the limb, such as a human forearm, receive a low amplitude vibration. The device is a vibratory splint which can be employed as a prophylactic intervention or as a modality directed toward the reduction of acute discomfort associated with RTS without the need to withdraw from concurrent activities. In addition, the device could be employed on other limbs and areas than the forearms, such as various positions on the leg. One such use could be in conjunction with orthotic devices utilized to support injured joints while another could be in the treatment of some pain problems associated with limb amputations. Nor, is the device necessarily limited to human use; horses for example, suffering from tendinitis in the foreleg could also be treated. Nonetheless, for purposes of the following description, the device shall be presented as utilized on the forearm.

A device according to the present invention is depicted in the drawings generally by the numeral 10. The device 10 comprises generally, a sleeve 12, adaptable to fit around the limb 11 of a living being; means for affixing the sleeve to the limb, indicated by the numeral 13; means for generating a low amplitude vibration, generally 14, carried by the sleeve; and, means for transmitting the vibrations generated to the limb, indicated by the numeral 15.

With reference to FIG. 1, the device 10 is depicted in use on the forearm of a person in position to decrease and thereby treat the pain brought about by repetitive trauma disorder (RTD). It has been found that certain repetitive motions or activities of the hand during working at a keyboard of a computer or the like, such as operation of the mouse, will result in pain in the forearm of the user caused by carpal tunnel syndrome and/or other syndromes associated with repetitive motion.

The sleeve 12 is somewhat flexible and is preferably pre-contoured to adapt readily to the human forearm. This accommodates variations in size while also providing a degree of stiffness or rigidity which aids in the treatment afforded by use of the device. The sleeve 12 is affixed to or mounted on the forearm with the use of fastening means 13, as will be described hereinbelow. While the sleeve is depicted on the right forearm, a device for the left arm would be the mirror image of the device 10. It will also be appreciated that the device can be manufactured in a plurality of sizes to provide a good fit about the desired limb.

Figure 2:
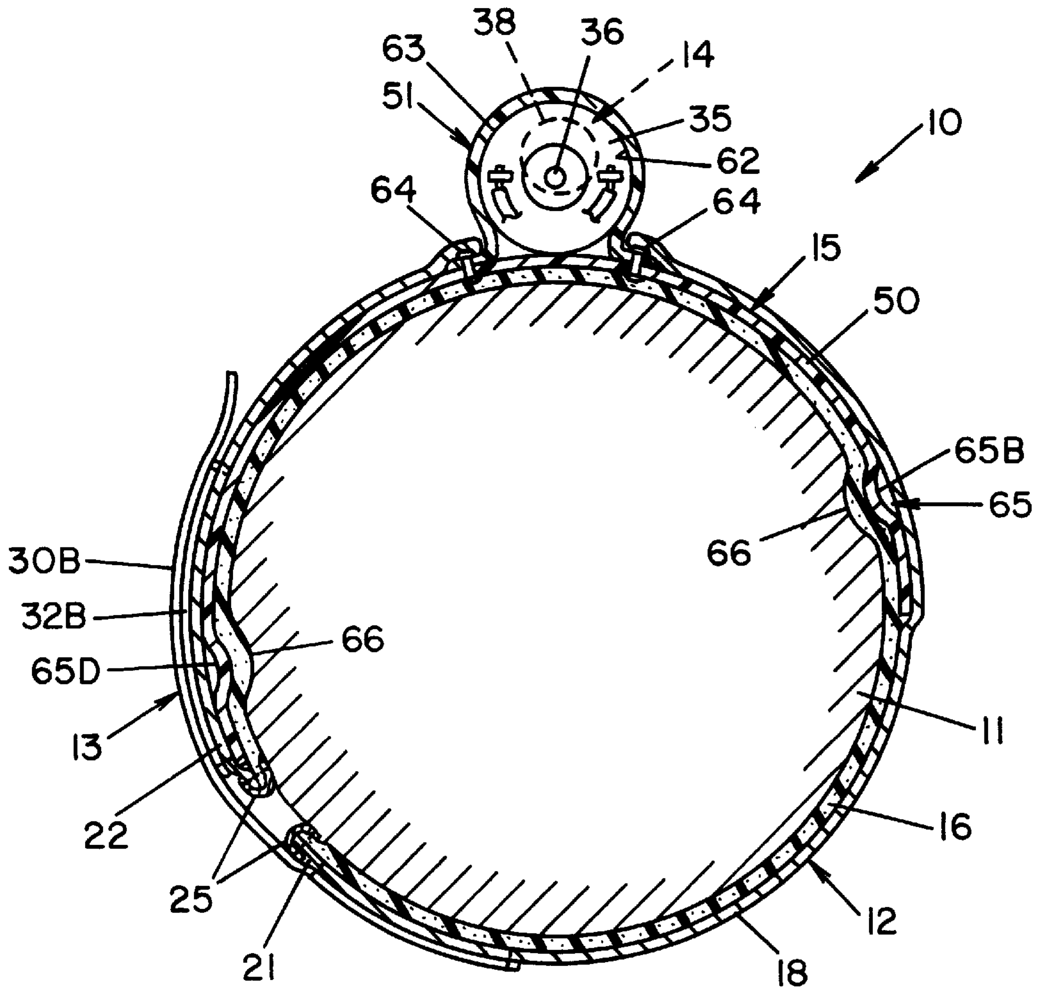
FIG. 2 is a cross sectional view taken substantially along the line 2—2 of FIG. 1, depicting the vibratory sleeve of the present invention.
Figure 4:
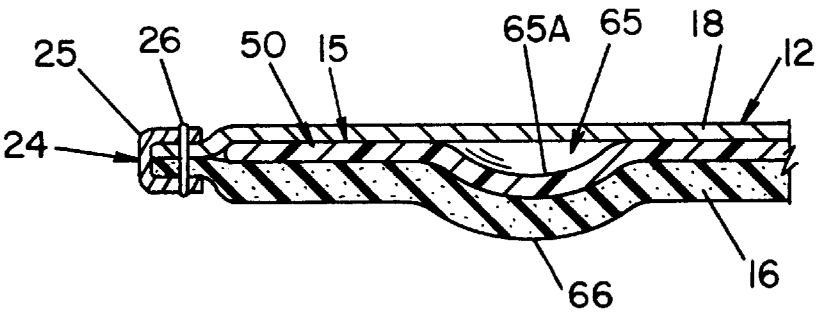
FIG. 4 is an enlarged cross sectional view, taken along the line 4—4 of FIG. 3, of the vibratory sleeve construction, depicting a molded nodule.

With reference to FIGS. 2 and 4, the sleeve 12 comprises an inner layer 16 and an outer layer 18. Inner layer 16 is preferably a soft foam material, such as polyethylene, Neoprene, polyurethane and the like, which will contact the forearm. Thickness of the foam layer is about one-sixteenth to about one-eighth of an inch, although the range is not critical. The outer layer 18 is preferably a vinyl layer, employed to provide a surface that is both aesthetic and readily cleaned. The two layers can be combined in a suitable fashion such as the use of a contact cement, known to those skilled in the art.

Figure 3:
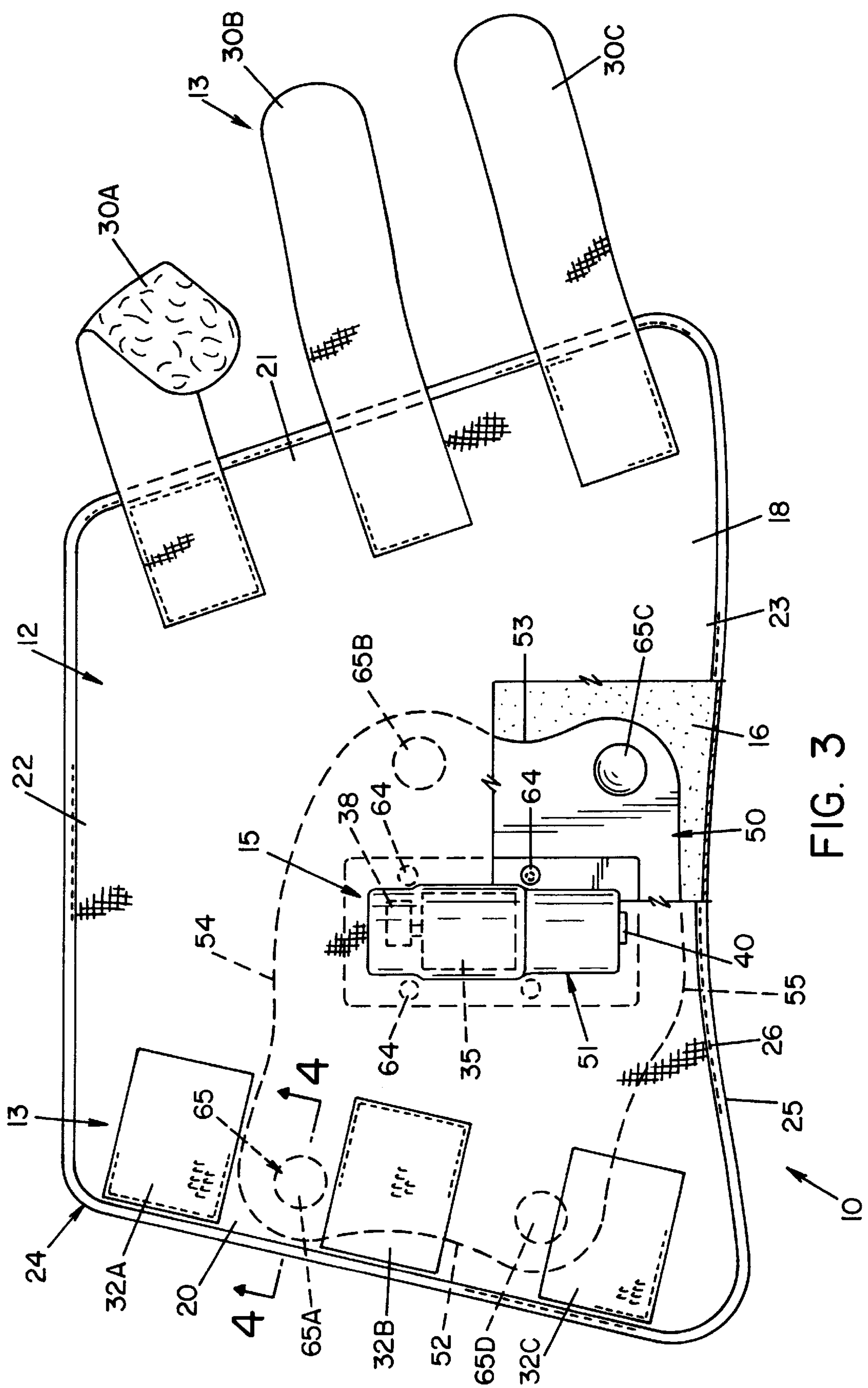
FIG. 3 is a developed view of the vibratory sleeve from the underside.

With reference to FIG. 3, the sleeve 12 provides a first lateral side 20, an opposed lateral side 21, upper or distal end 22 and lower or proximal end 23. A circumferential edge 24 joins the sides 20, 21 and ends 22, 23. As viewed in FIG. 4, the edge 24 comprises a tape or strip of vinyl 25, which is affixed by stitching 26, heat welding, adhesive or the like, to provide a smooth finished edge. For convenience of mounting the device on a limb, the sleeve is open.

Fastening means 13, as depicted in the drawings, include a plurality of strips 30A–30C and a like number of pads 32A–32C, each strip and pad forming a pair. The pads are provided near the first side 20 and the strips extend from the opposite side 21. The fastening means 13 preferably comprise a quick fastening/removal design such as Velcro. Accordingly, the pads 32A–32C carry a series of hooks, while the strips 30–30C carry the loops, although the hooks and loops could be reversed. Fastening about the forearm is completed by wrapping the device partially around and then cinching the hooks and loops together for a tight but comfortable fit. As noted hereinabove, the device is somewhat rigid and pre-contoured so as to accommodate the limb and, as will be explained hereinbelow, it should fit firmly so that the vibrations generated will be transferred to the affected area. It is also to be appreciated that while the foregoing fastening means comprise three strips and mating pads, that the present invention could employ at least one large flap and mating pad. A combination of elastic strips and/or an elastic or expandable sleeve could also be employed. Additionally, other fastening means such as snaps, buckles and the like could readily be substituted without affecting operation of the device. Moreover, if a closed, expandable sleeve were provided, fastening means, per se, could be eliminated.

Figure 5:
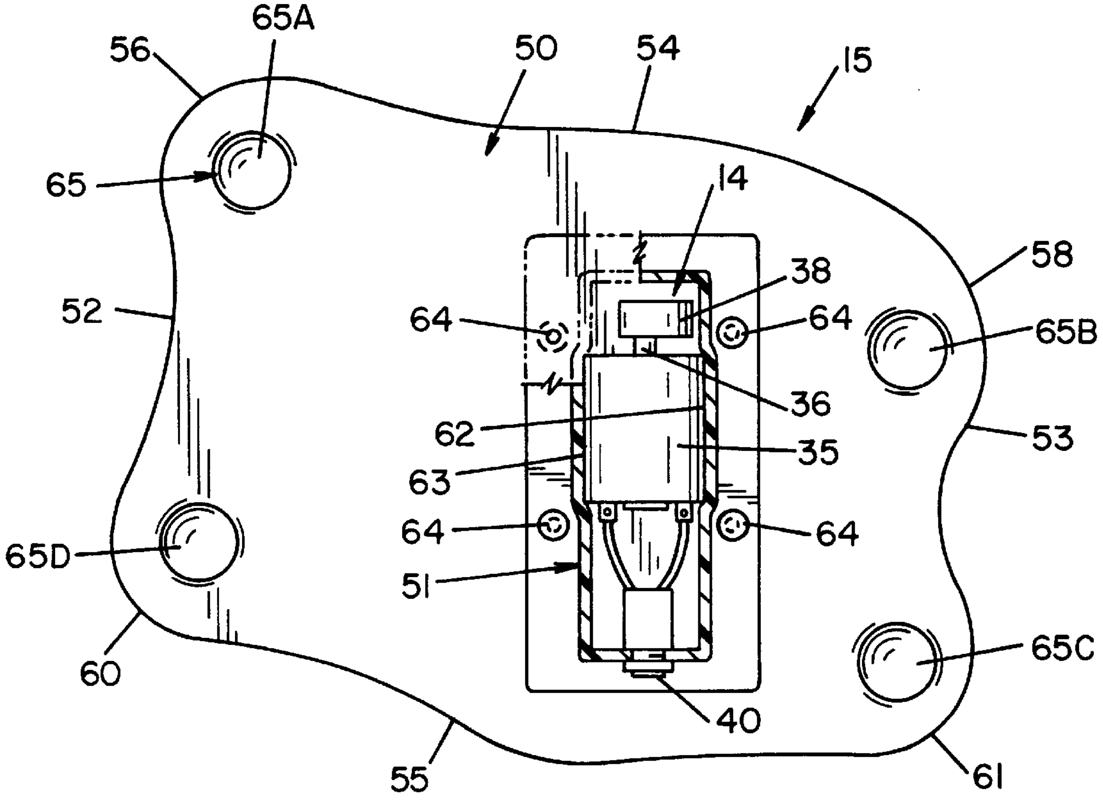
FIG. 5 is a plan view of a plate for the mounting of one means of vibration generator, according to the present invention.

A means for generating a vibration 14, according to the present invention is a small electric motor 35 which has an output shaft 36 to which a small weight metal slug 38, is affixed in an off-center fashion, as best depicted in FIG. 5. Spinning of the slug 38 creates the necessary vibration. A useful frequency of vibration for the device 10 has been found to be from about 64 to 84 Hz, with an amplitude of between 0.1 to 0.19 cm. Such a motor is manufactured by Mabuchi, model RE-260RA-2670, operating on 1.5 to 3 volts, and producing revolutions in the range of from about 5300 to 12,300 rpm, under no load and from about 5000 to 10,100 rpm under load. The motor 35 is wired to a simple female phone plug 40 for attachment to a cord 41, providing a male plug 42, from either a 3 volt AC/DC converter 43 or a battery pack 44, for portable use, containing two AA batteries. An on-off switch (not shown) can be provided as a more facile means of activating the device than connecting the phono plug 42 for operation.

The slug 38 is preferably brass and for the size of motor herein defined, it measured about 0.3 inch in length by about 0.5 in diameter. It was offset approximately 0.12 inch on the drive shaft, as noted hereinabove, in order to produce a suitable vibration. It is to be appreciated that neither size nor type of motor 35 is a limitation of the present invention, as is also true for the dimensions of slug 38; rather the foregoing specifications have been disclosed merely for purposes of enablement. Similarly, it is also to be appreciated that other means for generating vibration 14 within the ranges specified could be substituted for the motor 35 and slug 38. What is important is that the vibration frequencies disclosed be provided by the combination or other means provided, for the device 10 to accomplish the objects of the present invention.

The means for transmitting the vibrations generated, indicated by the numeral 15, comprises a semi rigid plate 50, and housing 51, within which the motor 35 is mounted. In the interest of maintaining a relatively light weight, the plate is of tough thermoplastic material, such as Surlyn 080, and it is also fashioned or pre contoured to fit the human forearm 11. In this fashion it is not necessary to apply undue force on the fastening means 13 and yet, there should be sufficient flexibility to accommodate variations in the size of forearms to which the device 10 is affixed. Rigidity is also necessary to transmit the vibrations as will become apparent hereinbelow.

The plate is generally sadle-shaped and is dimensioned so that with the curvature, it covers approximately one-half of the forearm 11. As most clearly depicted in FIG. 5, plate 50 provides opposed sides 52 and 53, left and right respectively, and distal (upper) edge 54 and proximal (lower) edge 55, sides 52 and 53 being curved concavely, while edges 54 and 55 are less pronounced. At the juncture of sides 52, 53 and edges 54, 55 are rounded corners. Corner 56, joining side 52 and edge 54, is sharper and more forward, or distal, than opposed corner 58, joining side 53 and edge 54. Similarly, corner 60, joining side 52 and edge 55, is sharper and more forward, or distal, than opposed corner 61, joining side 53 and edge 55. In this manner, side 52 extends somewhat more forward or distal on the ventral side of the limb while side 53 is somewhat more proximal on the dorsal side of the limb, as viewed in FIG. 1, where plate is depicted in phantom. The significance of this configuration will be discussed hereinbelow.

With reference to FIG. 2, the housing 51, is rigid and is again preferably of plastic, to minimize weight. Housing 51 provides an inside diameter 62 which conforms to and contacts the outer diameter or configuration of the motor 35, as at 63. A plurality of rivets 64, are provided to affix the motor 35 and its housing 51 to the plate 50. Because of the fit within the housing 51 and the rigidity of the plate and housing, the vibrations generated by revolution of the off-centered slug 38 are transmitted to the plate 50 and, in turn, to the forearm of the user In this manner, a low amplitude vibration is imparted by the device 10, directly to the soft tissues of the arm, providing a massage.

In order to increase the effect of the vibrations transmitted and provide somewhat of a localized delivery, at least one nodule 65 is provided in the plate 50 during manufacture. Nodule 65 is a concave depression, directed radially inwardly from the curvature of the plate 50 and measuring approximately ⅝ inch in diameter and protruding about $\frac{3}{16}$ inch from the underside of said plate. In FIGS. 2 and 4, it is seen that the nodule contacts the inner foam layer 16 and provides a pressure point, as at 66, against the forearm 11. Preferably, the device 10 carries a plurality of nodules 65A–65D, four being depicted in the drawings, at approximately the corners 56, 58, 60 and 61 of plate 50, respectively. Although other configurations are possible, it is preferred to provide at least one opposed pair of nodules 65A, 65B, or 65C, 65D, so as to transmit vibrations to opposite areas of the affected forearm.

The plate 50 and assembled motor 35 and housing 51 are assembled by cementing them as a unit between the vinyl outer layer 18 and foam inner layer 16. As depicted in FIG. 3, the plate is located toward the pads 32A–32C and near the proximal or lower edge 23 of the sleeve 12. This location allows concentration of the vibrations generated to the area of the limb where they will be most effective.

The method for treatment of RTS, according to the present invention includes the step of affixing the device 10 to the forearm 11 and switching on power to the motor 35, directly while engaging in the work or other activity that brings on the discomfort. In actual use of the device 10, the plate 50 and nodules 65A–D, carried thereby are positioned over the region of the extensor muscle origins (nodule 65D), the dorsal interosseus nerve (nodule 65B), and, the ulnar and median nerves, (nodule 65A) and (nodule 65C), respectively, of the forearm. In similar fashion, devices 10 for other uses would provide a plate 50 and position of nodule(s) to concentrate vibrations to muscles and nerves that require relief or would otherwise benefit from the stimulation.

In actual testing, it was found that pain attributed to the repetitive use of a computer pointing device, a mouse, was alleviated by generating and transmitting vibrations to the forearm for at least about 10 minutes as needed, as well as for longer periods of time, until pain abated. By wearing the device, which not only provides support for the soft tissue of the forearm but also applies low amplitude vibration directly to the areas beneath the nodules and indirectly to the area of the forearm beneath the plate 50, it was found that the forearm could remain engaged in the activity for longer periods of time than before the device was utilized, generally for as long as the wearer wished to pursue that activity, which could be several hours including the duration of a work shift. As a result, by use and operation of the device 10, it is now possible for workers, hobbyists and the like to maintain movements of the forearm without suffering from the pain attributed to RTS.

As should be appreciated, the configuration and construction of the device 10 allows it readily to adapt to the anatomy of any limb to which it will be affixed. Although the device 10 has been described in conjunction with treatment of the forearm, it is within the scope of the present invention to employ the device, appropriately configured to other limbs, as well as those of other living creatures, such as livestock and pets. The device can readily be manufactured in sizes to accommodate males and females as well as adults and children taking into account the fit about the limb and, the placement of the nodules.

Use of the device 10 hopefully eliminates the need for more invasive or restricting modalities decrease symptoms and/or eliminate symptoms of RTS and allow people to pursue vocational and avocational activities as they desire. More importantly, use of the device 10 can avoid carpal tunnel surgery which is one of the more invasive methods of medical treatment. Moreover, the present invention is also wearer friendly and does not require a high degree of manual dexterity to don and doff.

Thus it should be evident that the device and method of the present invention are highly effective in alleviating the pain associated with RTS. The invention is particularly suited for use on the forearm but is necessarily limited thereto. Occupations at risk for RTS other than computer users include users of business equipment, check out clerks, truck and bus drivers and workers utilizing their hands in arms in repetitive gripping movements, such as encountered in the food processing industry.

Based upon the foregoing disclosure, it should now be apparent that the use of the device described herein will carry out the objects set forth hereinabove. It is, therefore, to be understood that any variations evident fall within the scope of the claimed invention and thus, the selection of specific component elements can be determined without departing from the spirit of the invention herein disclosed and described. In particular, devices according to the present invention are not necessarily limited to those employing a 3 volt motor as disclosed. Moreover, as noted hereinabove, other means for generating vibrations can be substituted for the motor. Thus, the scope of the invention shall include all modifications and variations that may fall within the scope of the attached claims.

What is claimed is:

1. A device for the delivery of low amplitude vibration to limbs comprising:
   - a flexible sleeve having inner and outer layers and adapted to fit circumferentially around the limb of a living being;
   - means for mounting said sleeve about the limb;
   - means for generating a low amplitude vibration, carried by said sleeve; and
   - means for transmitting said vibrations to the limb, comprising a plate and a housing, said housing being in contact with said means for generating a vibration, wherein said plate is secured between said outer layer and said inner layer of said sleeve and said housing is secured to said plate; said plate, housing and means for generating being affixed together; and
   - wherein said mea ns for transmitting further provides at least one nodule extending from said plate, impinging against said inner layer of said sleeve.

2. A device for the delivery of low amplitude vibration, as set forth in claim 1, wherein said sleeve inner layer is foam and is positionable against the limb, and said outer layer is vinyl and provides opposed sides and distal and proximal edges.

3. A device for the delivery of low amplitude vibration, as set forth in claim 2, wherein said means for mounting comprises at least one strip affixed to one of said edges on said outer layer and at least one attachment panel affixed to said other edge and said outer layer, said strip and attachment panel providing a hook and loop system of adhering together to accommodate a range of diameters.

4. A device for the delivery of low amplitude vibration, as set forth in claim 1, wherein said means for generating a vibration includes a motor having an output shaft and a weight carried off center on said shaft.

5. A device for the delivery of low amplitude vibration, as set forth in claim 1, wherein said plate provides opposed surfaces, lateral sides and distal and proximal edges, said sides and edges being joined together by corners.

6. A device for the delivery of low amplitude vibration, as set forth in claim 5, wherein said nodule extends from said plate on the other of said opposed surfaces.

7. A device for the delivery of low amplitude vibration, as set forth in claim 1, said means for transmitting providing a pair of said nodules on said plate.

8. A device for the delivery of low amplitude vibration, as set forth in claim 1, wherein said means for generating provides a frequency of vibration ranging from about 64 to 84 Hz with an amplitude of about 0.1 to 0.2 mm.

9. A method for the treatment of repetitive trauma syndrome comprising:

affixing a device providing a flexible sleeve circumferentially about the limb affected and transmitting a low amplitude vibration from said device to said limb;

wherein said device comprises said flexible sleeve having inner and outer layers;

means for mounting said sleeve about said limb;

means for generating a low amplitude vibration, carried by said sleeve; and means for transmitting said vibrations to said limb, comprising a plate and a housing, said housing being in contact with said means for generating a vibration, said plate, housing and means for generating being affixed together;

wherein said means for transmitting further provides at least one nodule extending from said plate, impinging against said inner layer of said sleeve.

10. A method for the treatment of repetitive trauma syndrome, as set forth in claim 9, wherein said step of transmitting provides said vibrations through said nodule.

11. A method for the treatment of repetitive trauma syndrome, as set forth in claim 9, said means for transmitting providing a pair of said nodules, on said plate.

12. A method for the treatment of repetitive trauma syndrome, as set forth in claim 11, wherein said step of transmitting provides said vibrations through said pair of nodules.

13. A device for the delivery of low amplitude vibration to limbs, comprising:

a flexible sleeve having inner and outer layers and adapted to fit circumferentially around the limb of a living being;

means for mounting said sleeve about the limb;

means for generating a low amplitude vibration, carried by said sleeve; and means for transmitting said vibrations to the limb, comprising a plate and a housing, said housing being in contact with said means for generating a vibration, said plate, housing and means for generating being affixed together;

wherein said means for transmitting further provides at least one nodule extending from said plate, impinging against said inner layer of said sleeve.

14. A device for the delivery of low amplitude vibration , as set forth in claim 13, wherein said sleeve inner layer is foam and is positionable against the limb, and said outer layer is vinyl and provides opposed sides and distal and proximal edges.

15. A device for the delivery of low amplitude vibration, as set forth in claim 13, wherein said means for mounting comprises at least one strip affixed to one of said edges on said outer layer and at least one attachment panel affixed to said other edge and said outer layer, said strip and attachment panel providing a hook and loop system of adhering together to accommodate a range of diameters.

16. A device for the delivery of low amplitude vibration, as set forth in claim 13, wherein said means for generating a vibration includes a motor having an output shaft and a weight carried off center on said shaft.

17. A device for the delivery of low amplitude vibration, as set forth in claim 13, said means for transmitting providing a pair of said nodules on said plate.

18. A device for the delivery of low amplitude vibration, as set forth in claim 13, wherein said means for generating provides a frequency of vibration ranging from about 64 to 84 Hz with an amplitude of about 0.1 to 0.2 mm.

* * * * *